United States Patent [19]

Kurkov

[11] 4,251,467
[45] Feb. 17, 1981

[54] CONTINUOUS PREPARATION OF CHLOROACETONE

[75] Inventor: Victor P. Kurkov, San Rafael, Calif.

[73] Assignee: Chevron Research Company, San Francisco, Calif.

[21] Appl. No.: 719,799

[22] Filed: Sep. 2, 1976

Related U.S. Application Data

[63] Continuation-in-part of Ser. No. 584,225, Jun. 5, 1975, abandoned, which is a continuation-in-part of Ser. No. 418,166, Nov. 21, 1973, abandoned.

[51] Int. Cl.³ .............................................. C07C 45/63
[52] U.S. Cl. ..................................... 568/393; 568/394; 568/411; 568/419
[58] Field of Search ................................... 260/593 H

[56] References Cited

U.S. PATENT DOCUMENTS

| 3,346,646 | 10/1967 | Kokarudy | 260/593 H |
| 3,397,240 | 8/1968 | Kaufan et al. | 260/593 H |

FOREIGN PATENT DOCUMENTS 707852 12/1930 France .................................. 260/593 H

OTHER PUBLICATIONS

Friend, Inorganic Chemistry, vol. VIII, pp. 224–230.

*Primary Examiner*—James H. Reamer
*Attorney, Agent, or Firm*—J. A. Buchanan, Jr.; C. J. Caroli; W. K. Turner

[57] ABSTRACT

Symmetrical 1,3-dichloroacetone is prepared by contacting chlorine with an aqueous mixture of acetone, monochloroacetone, or mixtures thereof and an iodine-containing promoter.

12 Claims, 2 Drawing Figures

CONTINUOUS PREPARATION OF CHLOROACETONE

CROSS-REFERENCE TO RELATED APPLICATION

This application is a continuation-in-part of U.S. application Ser. No. 584,225, filed June 5, 1975 now abandoned, which, in turn, is a continuation-in-part of application Ser. No. 418,166, filed Nov. 21, 1973, now abandoned.

BACKGROUND OF THE INVENTION

This invention relates to preparation of symmetrical dichloroacetone. More particularly, the invention is concerned with a superior new method of preparing symmetrical 1,3-dichloroacetone in improved yields utilizing continuously regenerated iodine chloride.

Dichloroacetone is useful as a cross-linking agent for polymers and wood pulp. It is also useful as a chemical intermediate in the preparation of germicides, fungicides and insecticides.

Chloroacetones have been prepared by chlorination of acetone according to various procedures. U.S. Pat. No. 2,635,118 discloses the preparation of di- and trichloroacetones by introducing chlorine and acetone into a mixture of di- and trichloroacetones. U.S. Pat. No. 3,265,740 discloses chlorination of acetone to the hexachloro derivative. U.S. Pat. No. 3,346,646 discloses the reaction of 1-chloro- or 1,1-dichloroacetone with aqueous hypochlorous acid solution to give 1,1,1-trichloroacetone. U.S. Pat. No. 3,397,240 discloses a process for making monohaloacetone and identifies overchlorinated by-products as 1,1-dichloroacetone and 1,3-dichloroacetone obtained in a ratio of about 2-4:1, respectively.

Symmetrical 1,3-dichloroacetone is particularly useful as a chemical intermediate because of the disposition of the chlorine substituent on the 1 and 3 positions. However, 1,3-dichloroacetone is difficult to prepare since direct chlorination of acetone leads to 1,1-dichloroacetone as the major product. More elaborate procedures of preparing 1,3-dichloroacetone include the reaction of 1,3-di-iodoacetone with silver chloride (Annalen 192, 93) by the chromic acid oxidation of symmetrical dichloroisopropyl alcohol (Berichte 4, 562) and by reaction of hydrochloric acid with chloroethoxyacetoacetic ester (Annalen 269, 18). The reaction of acetone and iodine chloride is disclosed in Z. fur chem., 1867, 375 and with iodine trichloride in Annalen, 192, 89.

SUMMARY OF THE INVENTION

The present invention encompasses a process for preparing improved yields of 1,3-dichloroacetone which comprises contacting molecular chlorine with an aqueous mixture of acetone, monochloroacetone, or mixtures thereof and an iodine-containing promoter.

DETAILED DESCRIPTION OF THE INVENTION

Although the present process is not restricted by any particular theory, the selectivity to 1,3-dichloroacetone is assumed to occur because of a sequence of steps:

(1) $MI + Cl_2 \rightarrow ICl + MCl$

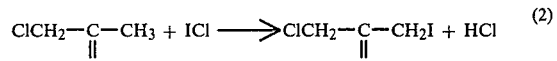

$$ClCH_2-\underset{\underset{O}{\|}}{C}-CH_3 + ICl \longrightarrow ClCH_2-\underset{\underset{O}{\|}}{C}-CH_2I + HCl \quad (2)$$

$$ClCH_2-\underset{\underset{O}{\|}}{C}-CH_2I + MCl \longrightarrow ClCH_2-\underset{\underset{O}{\|}}{C}-CH_2Cl + MI \quad (3)$$

In describing the invention, conventional terminology is used. The word "iodide" is used to denote the negative iodine anion, $I^-$. The term "molecular iodine" is used to denote the diatomic iodine molecule, $I_2$. The word "iodine" is used generically to refer to either the anionic or molecular iodine, and is also used to name particular compounds such as iodine chloride, ICl. Corresponding definitions apply to "chloride", "molecular chlorine", and "chlorine".

Accordingly, water-soluble iodine-containing promoters include iodine and both salts and protonic acids of iodine, which upon reaction with molecular chloride give ICl. Thus, in the above equations M is hydrogen, ammonium, or a metal having water-soluble chlorides and iodides. Water-soluble metal chloride salts and iodide salts are those in which 3.0 grams of the chloride and iodide compound are soluble in 100 grams of water at 20° C., or which are indicated to be soluble(s) in a handbook such as Lange's 9th Edition *Handbook of Chemistry*, pages 212 to 333. For example, the alkali metal salts such as the lithium, sodium, potassium and cesium salts; the alkaline earth metal salts such as magnesium, calcium, beryllium and barium salts; the transition metal salts such as cobalt, manganese, nickel, iron and zinc salts; and the ammonium salts are suitable water-soluble iodine-containing promoters. The alkali metal salts, especially the lithium and potassium salts, are preferred water-soluble iodine-containing promoters. Representative iodide-containing promoters are also described in U.S. Pat. No. 3,816,488, granted June 11, 1974; U.S. Pat. No. 3,944,604, granted March 16, 1976; and U.S. Pat. No. 3,956,407, granted May 11, 1976. (The descriptions contained in these patents are incorporated herein by reference.)

Another source of iodine-containing promoters is the organic iodine compounds with displaceable I, e.g., $CH_3I$, iodoacetone, iodoacetic acid, $CH_2I_2$, $ICH_2CH_2I$, etc. The aforementioned compounds can undergo a nucleophilic displacement reaction with a chloride ion to generate an iodide ion and an organic chloride as exemplified in equation (3).

It is theorized that steric hindrance prevents the formation of 1-iodo-1-chloroacetone in reaction (2). The reaction is thereby directed to the formation of 1-iodo-3-chloroacetone. Direct chlorination, which tends to give the 1,1-dichloroacetone, as mentioned above, is inhibited by the fast oxidation of the iodide anion by molecular chlorine in the aqueous phase to form (regenerate) ICl and chloride ions in accordance with equation (1).

Iodine chloride (ICl) is essential to the selective formation of 1,3-dichloroacetone. As illustrated by equation (1) above, ICl is continuously generated during reaction. However, ICl may be added to initiate the process. In addition, either molecular iodine ($I_2$) or $ICl_3$ may be used with good results.

The preferred feed in the process in accordance with this invention is usually acetone because it is readily available. However, mixtures of acetone and monochloroacetone are also satisfactory feedstocks. 1,3-dichloroacetone may also be obtained from monochloroacetone by this process.

Water is essential as the reaction medium. The quantity of water may vary broadly but is generally in the range of 0.3 to 100, preferably 1 to 10, volumes of water per volume of acetone and/or monochoroacetone. For most of the reaction, two phases consisting of an organic phase and an aqueous phase are present. Organic media such as acetic acid form a homogenous reaction phase, but under comparable reaction conditions the ratio of 1,3-dichloroacetone to 1,1-dichloroacetone drops from about 17 to about 2. In the absence of water medium, acid-catalyzed condensations of acetone to mesityl oxide, isophorone, etc., take place, thereby causing a loss in yield.

The temperature of the reaction is correlated with the desired reactivity of molecular chlorine. For present purposes the temperatures range from about 15° C. to about 80° C. As the temperature of the reaction is increased, the selectivity of 1,3-dichloroacetone decreases due to the fact that as the temperature goes up the reactivity of molecular chlorine increases, and it reacts with monochloroacetone in a direct, random fashion without going through the iodine intermediate. Also at higher temperatures, in excess of about 50° C., some trichloroacetone by-product is formed.

The chlorine in the reaction is in an amount at least sufficient to provide the dichloroacetone—that is, at least about 2 mols of chlorine per mol of acetone is used. The rate of chlorine addition is correlated with the temperature of the reaction and the total iodine concentration for optimum selectivity. It has been found that under comparable conditions the selectivity of 1,3-dichloroacetone formation drops as the rate of chlorine addition is increased, but the rate of chlorine addition may be increased without drop in selectivity, so long as there is sufficient total iodine present to react with the added chlorine to form iodine chloride, which then iodinates the acetone as outlined in the above equations.

The reaction times in the present process are those sufficient to provide the desired chlorination of acetone or mixtures thereof with monochloroacetone to 1,3-dichloroacetone. In view of the relationship of the chlorine addition and iodine promoter discussed above, shorter reaction times are possible with the use of increased amounts of iodine-containing promoter. With large quantities of iodine in the system, it is preferred to have a water-soluble metal chloride dissolved in the water. In such cases the chloride salt is preferably in excess to the total iodine concentration (on a molar basis) to ensure sufficient chloride ion concentration for the reaction.

In the preparation of symmetrical 1,3-dichloroacetone in accordance with the process of the present invention the ratio of 1,3-dichloroacetone to 1,1-dichloroacetone is in excess of 2, usually greater than 4 and in some instances as high as 15 or 20 or more.

The dichloroacetone-containing mixture obtained from the reaction zone may be purified by various means. The first step is generally separation into an aqueous phase and an organic phase by the usual liquid phase separation techniques. Then the organic phase is further purified. According to one method, the monochloroacetone is first removed, preferably by distillation. The residual mixture of 1,1- and 1,3-dichloroacetone is effectively separated by crystallization since 1,3-dichloroacetone has a melting point of 45° C. compared to the 1,1-isomer, which is a liquid at ambient temperatures. Distillation, under reduced pressure if necessary, is also an effective means of separation, because the two isomers have greatly different boiling points—this is, 120° C. for the 1,1-isomer versus 173° C. for the 1,3-isomer.

DESCRIPTION OF THE DRAWINGS

The accompanying drawings show schematic flow diagrams of cyclic processes for the preparation of 1,3-dichloroacetone utilizing a preferred continuous processing as shown in FIG. 1, and also a process for continuous regeneration of iodine chloride by the addition of chlorine to an aqueous recycle phase containing iodide salt and little, if any, chloroacetone as shown in FIG. 2.

The preferred mode of carrying out the process of this invention is via a continuous process as shown schematically in FIG. 1. In this process, fresh acetone, monochloroacetone or mixtures thereof and any make-up water are charged via line 4. These components are combined with recycle water, acetone, monochloroacetone, iodide and chloride salts of line 5 and passed into the reactor 1 via line 6. Chlorine gas is charged via line 7. The reactor in which chlorination occurs may be a stirred vessel having a constant level overflow device and a gas release line 8 for any excess HCl. The reaction mixture after a predetermined average residence time passes out of the reactor via line 9 into a quiescent separation zone 2. In this zone, the heavy organic phase settles to the bottom and is removed through line 13. The less dense aqueous phase passes out of the separation zone via line 10. Line 11 is provided to remove sufficient aqueous recycle to prevent an unlimited build-up of water-soluble impurities or by-products. The main portion of the aqueous phase, however, passes through line 12, is combined with the acetone and monochloroacetone of line 16 and recycled back to the reactor via lines 5 and 6. The organic phase in line 13 is charged to distillation zone 3. In this zone, low boiling acetone and monochloroacetone are distilled out and removed through line 14. Line 15 is provided to remove all or a portion of this fraction. Preferably, a small portion will be withdrawn to prevent the build-up of water-insoluble, low-boiling impurities, and the remainder is recycled to the reactor via lines 16, 5 and 6. The bottoms from the distillation zone is removed through line 17. It consists predominantly of 1,3-dichloroacetone, which may be further purified, for example, by crystallization.

Figure 1:
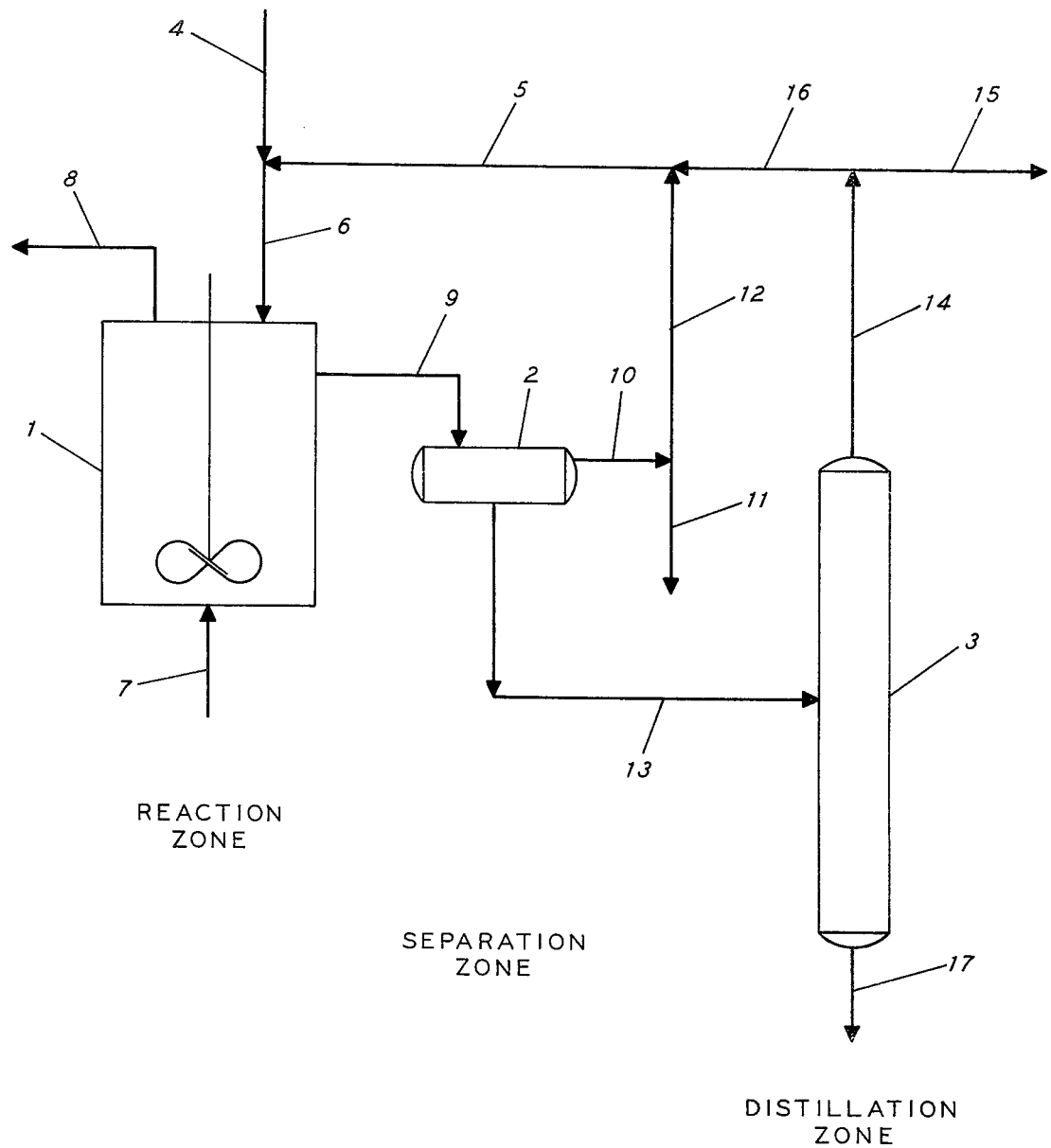
Figure 2:
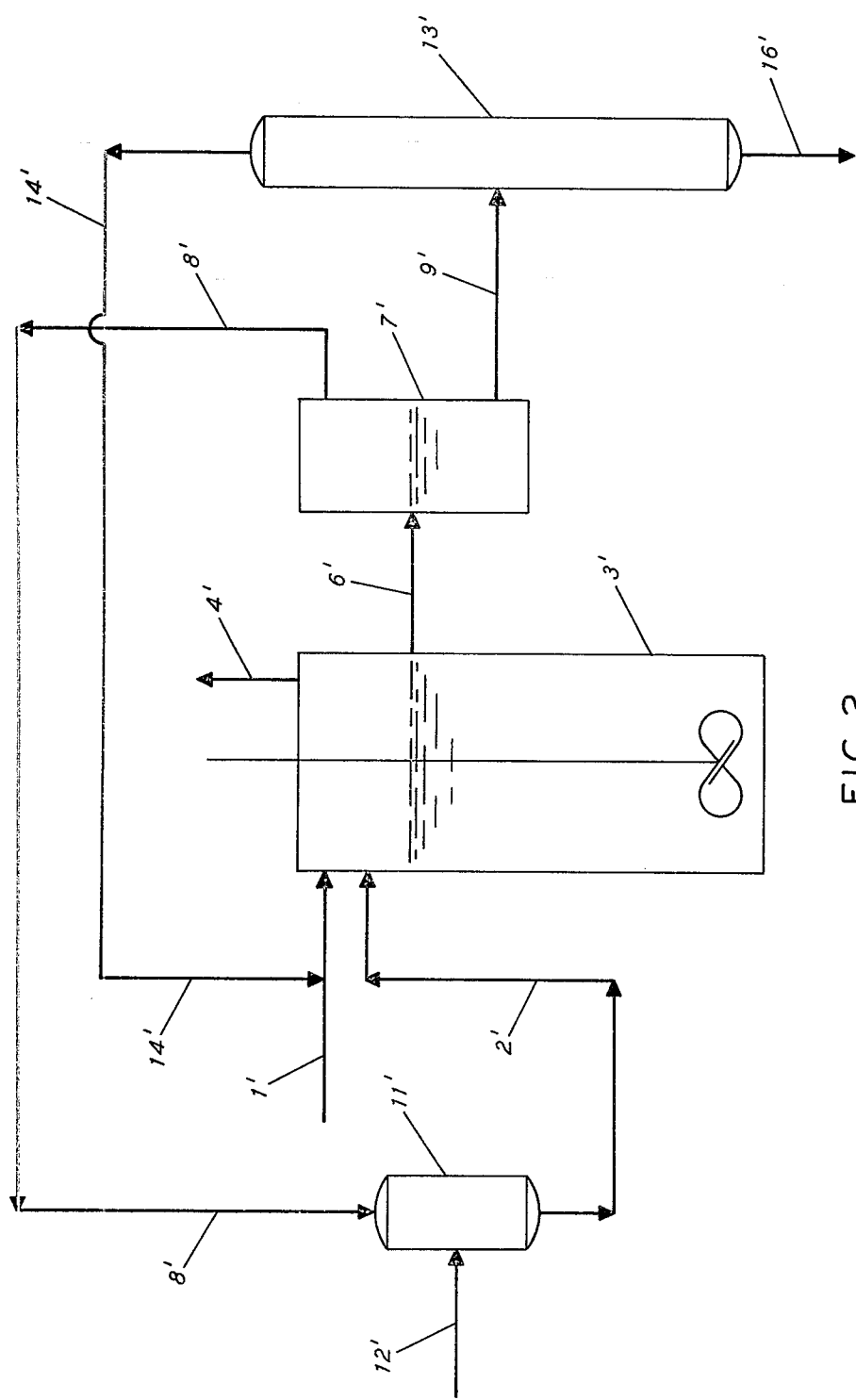
Turning to FIG. 2 of the drawings, acetone, monochloroacetone, or mixtures thereof are introduced to the reaction via line 1' along with iodine chloride and aqueous solution of a water-soluble metal chloride via line 2' into stirred chlorinator 3'. Hydrogen chloride is vented from the chlorinator at 4', and the reaction mixture is withdrawn via line 6' into phase separator 7'. In the phase separator an aqueous phase containing most of the iodine, iodide and chloride salt is withdrawn and recycled via line 8' to oxidizer 11'. Chlorine is introduced via line 12' to regenerate the iodine chloride, following which the mixture of chlorine, iodine chloride, water-soluble chloride, and water is recycled to stirred chlorinator 3'. An organic phase is withdrawn from phase separator 7' via line 9'. This organic phase contains essentially all unreacted acetone and chlorinated acetones, including 1,3-dichloroacetone product, into separator 13'—for example, a distillation column. From separator 13' acetone and monochloroacetone are withdrawn through line 14' and recycled via line 1' to stirred chlorinator 3'. Dichloroacetones, which are primarily 1,3-dichloroacetone, are withdrawn as product via line 16' and may be subjected to further purification as desired—for example, crystallization or distillation to remove the 1,1-dichloroacetone isomer, which has greatly dissimilar melting points and boiling points (liquid at room temperature compared to melting point of 45° C., and boiling point of 120° C. compared to 173° C., respectively, for the 1,1-isomer versus the 1,3-isomer).

Although the above embodiment of the process of the invention lies in the use of aqueous phase recycle to a separate oxidizer where iodide salt is reacted with chlorine to give iodine chloride without chlorine directly contacting acetone, the oxidizer and chlorinator may be combined in a single reactor. So long as iodide salt is continuously and preferably converted into iodine chloride by contacting with chlorine, the acetone and monochloroacetone will react with the iodine chloride to produce symmetrical 1,3-dichloroacetone rather than the 1,1-dichloroacetone ordinarily produced by direct reaction with chlorine.

EXAMPLES

The following examples are further illustrative of the process of preparing symmetrical 1,3-dichloroacetone in accordance with the present invention. Unless otherwise specified, the proportions in the illustrative examples are on a molar basis and the product analysis is by NMR spectrometry.

EXAMPLE 1

A 250-ml round-bottom flask (RBF) equipped with a stirrer, thermometer, reflux condenser, and a gas inlet tube was charged with 50 ml (0.68 mol) of acetone, 100 ml of water, 33 grams (0.21 mol) of iodine chloride, and 30 grams (0.7 mol) of lithium chloride. This mixture was stirred at room temperature for 18.5 hours, during which time chlorine gas was added at a rate of 0.12 mol per hour. Periodically, a small aliquot was analyzed by NMR. At three and one-quarter hours, conversion of acetone was 79%; and about 55% of the product was monochloroacetone. At 18½ hours, conversion was 100%; and the product contained 4.6% monochloroacetone, 20% trichloroacetone, and 75.4% dichloroacetone in an 18:1 ratio of 1,3-dichloroacetone: 1,1-dichloroacetone.

Chloroform, 150 ml, was added to the reaction product. The resulting mixture was filtered, and then the two layers were separated. The aqueous layer was extracted two times with 50 ml of chloroform. The extracts were added to the chloroform layer. The combined chloroform solution was washed with a concentrated sodium thiosulfate solution and, after drying, was evaporated to give 92.8 grams of chloroform-free, oily reaction product. This oil was washed three times with 800 ml of pentane to give 65.9 grams of white crystalline, 1,3-dichloroacetone, a 77% yield. NMR indicated it to be a pure compound.

EXAMPLE 2

To the same apparatus as in Example 1, there was charged 50 ml (0.68 mol) of acetone, 100 ml of water, and 17.8 grams (0.07 mol) of iodine. The resulting mixture was stirred at room temperature for 50 hours, during which time gaseous chlorine was added at the rate of 7.2 ml per minute. At the end of the reaction time, NMR analysis showed the reaction product to contain no acetone but 53.8% monochloroacetone and 46.2 dichloroacetone in a 15:1 ratio of the 1,3-isomer to the 1,1-isomer.

In a workup similar to that of Example 1, there was obtained 87.6 grams of crude product from which 36.5 grams of white crystals of 1,3-dichloroacetone were obtained.

EXAMPLE 3

A 100-ml RBF was charged with 90 g (0.546 mol) of ICl dissolved in 500 ml of water. Then 100 ml (1.36 mols) of acetone was added and the mixture was heated to 70° C. After 4 hours at this temperature, the reaction mixture was cooled to ambient temperature, whereupon it was separated into two phases. The lower phase was removed, washed with water, and dried over $Na_2SO_4$. An NMR spectrum of the dried product gave the following composition as compared to known compounds: 84% monoiodoacetone, 15% monochloroacetone, and 11% 1,3-dichloroacetone (percentages based upon reacted acetone). An IR spectrum showed a strong absorption at 1700 $cm^{-1}$.

EXAMPLE 4

A 500-ml RBF was charged with 120 ml of water, 35 g (0.84 mol) of lithium chloride, 90 g (0.55 mol) of ICl and 15.7 g (0.272 mol) of acetone. The entire mixture was stirred for 30 hours at 25° C. Aliquots were removed periodically for NMR analysis. After 6 hours, anly a small amount of reaction had occurred; at 22 hours, about 9% 1,3-dichloroacetone had formed; and at 30 hours, the acetone was 96% converted into products as follows: 7% monoiodoacetone, 72% monochloroacetone, 16% 1,3-dichloroacetone, and 5% 1-chloro-3-iodoacetone.

Examples 3 and 4 show the formation of 1,3-dichloroacetone in the absence of additional chlorine. Greatly improved yields of 1,3-dichloroacetone are obtained by the process of the present invention, as shown by Examples 1 and 2.

Although the process of the invention has been described with respect to the preparation of symmetrical 1,3-dichloroacetone by the chlorination of acetone, other analogous halogenation reactions are included. For example, it is contemplated that symmetrical 1,3-dibromoacetone may be prepared by the same basic procedures.

While the character of this invention has been described in detail with numerous examples this has been done by way of illustration only and without limitation of the invention. It will be apparent to those skilled in the art that modifications and variations of the illustrative examples may be made in the practice of the invention within the scope of the following claims.

What is claim is:

1. A process of preparing 1,3-dichloroacetone which comprises contacting molecular chlorine with an aqueous mixture of acetone, monochloroacetone, or mixtures thereof and an iodine-containing promoter.

2. A process in accordance with claim 1 in which the iodine-containing promoter is converted into iodine chloride by the reaction with chlorine.

3. A process in accordance with claim 2 in which the aqueous mixture comprises acetone and a water-soluble iodine-containing promoter.

4. A process according to claim 1 in which the water-soluble iodine-containing promoter is selected from the group consisting of hydrogen iodide, alkali metal iodides, alkaline earth metal iodides, transition metal iodides, and ammonium iodide.

5. A process according to claim 1 in which the iodine-containing promoter is selected from the group consisting of iodine, iodine chloride, iodine trichloride and organic iodine compounds.

6. A process for the preparation of 1,3-dichloroacetone which comprises contacting molecular chlorine with an aqueous mixture of acetone, monochloroacetone, or mixtures thereof, and a water-soluble iodine-containing promoter; charging the chlorinated reaction mixture to a liquid phase separation zone; separating the upper, aqueous phase from the lower organic phase; recycling said upper chase to the chlorination reaction zone; recovering 1,3-dichloroacetone from said lower phase.

7. A process in accordance with claim 6 in which the acetone, monochloroacetone, or mixtures thereof are reacted with iodine chloride at temperatures of about 15° C. to about 80° C.

8. A process in accordance with claim 7 in which monochloroacetone in the reaction product is removed by distillation.

9. A process in accordance with claim 8 in which 1,3-dichloroacetone is separated from the reaction product by crystallization.

10. A process in accordance with claim 6 in which the iodine-containing promoter is selected from the group consisting of iodine, hydrogen iodide, iodine chloride, iodine trichloride, ammonium iodide, soluble metal iodides, iodoacetone, iodoacetic acid, diiodomethane, and diiodoethane.

11. A process in accordance with claim 1 which comprises contacting acetone, monochloroacetone, or mixtures thereof with continuously regenerated iodine chloride in an aqueous solution of a water-soluble chloride; separating an aqueous phase containing iodide salt, and an organic phase containing the chlorinated acetones including 1,3-dichloroacetone; adding chlorine to the separate aqueous phase to regenerate iodine chloride from iodide salt; recycling the aqueous regenerated iodine chloride and water-soluble chloride to the reaction zone; withdrawing 1,3-dichloroacetone product from the separate organic phase; and recycling unreacted acetone and monochloroacetone to the reaction zone.

12. A process according to claim 11 in which the chloride is selected from the group consisting of hydrogen chloride, alkali metal chlorides, alkaline earth metal chlorides, transition metal chlorides, and ammonium chloride; and the iodine-containing promoter is selected from the group consisting of iodine, hydrogen iodide, iodine chloride, iodine trichloride, ammonium iodide, water-soluble metal iodides, iodoacetone, iodoacetic acid, diiodomethane, and diiodoethane.

* * * * *